United States Patent
Uchida et al.

(10) Patent No.: US 8,993,650 B2
(45) Date of Patent: Mar. 31, 2015

(54) MIXABLE AND COLOR TONE FREELY REPRODUCIBLE DENTAL COLORING MATERIAL COMPOSITION, AND SET AND METHOD THEREOF

(75) Inventors: Jun Uchida, Kyoto (JP); Yushin Okimoto, Kyoto (JP); Mitsuji Teramae, Kyoto (JP); Mitsuharu Mizuno, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 582 days.

(21) Appl. No.: 12/458,141

(22) Filed: Jul. 1, 2009

(65) Prior Publication Data

US 2010/0081728 A1    Apr. 1, 2010

(30) Foreign Application Priority Data

Oct. 1, 2008    (JP) .................. 2008-256427

(51) Int. Cl.
*A61K 6/08*    (2006.01)
*A61K 6/00*    (2006.01)

(52) U.S. Cl.
CPC ............. *A61K 6/0094* (2013.01); *A61K 6/0002* (2013.01); *A61K 6/0097* (2013.01); *A61K 6/0058* (2013.01); *A61K 6/08* (2013.01)
USPC ....................................................... 523/105

(58) Field of Classification Search
CPC ..... A61K 6/08; A61K 6/0002; A61K 6/0058; A61K 6/0094; A61K 6/0097
USPC ........................................................ 523/105
See application file for complete search history.

(56) References Cited

U.S. PATENT DOCUMENTS

| | | | |
|---|---|---|---|
| 5,013,629 A * | 5/1991 | Sekine et al. | 430/138 |
| 5,151,520 A * | 9/1992 | Gottschalk et al. | 126/638 |
| 6,528,555 B1 * | 3/2003 | Nikutowski et al. | 523/116 |
| 2002/0198284 A1 * | 12/2002 | Nakatsuka et al. | 523/116 |
| 2004/0138330 A1 | 7/2004 | Grundler et al. | |
| 2005/0123880 A1 | 6/2005 | Grundler et al. | |
| 2005/0168550 A1 * | 8/2005 | Deckers et al. | 347/100 |
| 2006/0004116 A1 * | 1/2006 | Kishi et al. | 522/146 |
| 2007/0122361 A1 * | 5/2007 | Jia | 424/53 |
| 2007/0148609 A1 * | 6/2007 | Brennan et al. | 433/9 |

(Continued)

FOREIGN PATENT DOCUMENTS

| | | |
|---|---|---|
| JP | 2-293849 | 12/1990 |
| JP | 2004-203865 | 7/2004 |

(Continued)

OTHER PUBLICATIONS

Office Action issued Jan. 15, 2013 in corresponding Japanese Application No. 2008-256427.

*Primary Examiner* — Michael Pepitone
(74) *Attorney, Agent, or Firm* — Wenderoth, Lind & Ponack, L.L.P.

(57) ABSTRACT

A dental coloring material composition comprising containing:
(a) a polymerizable monomer and/or an oligomer,
(b) a polymerization catalyst, and
(c) a pigment and/or a dye, wherein a color tone thereof is a cyan color based on three subtractive primary colors, or a color tone thereof is a magenta color based on three subtractive primary colors, or a color tone thereof is a yellow color based on three subtractive primary colors, and a dental color material set using the dental coloring material compositions in combination.

21 Claims, 3 Drawing Sheets

(56) References Cited

U.S. PATENT DOCUMENTS

2009/0081420 A1* 3/2009 Tojo et al. .................. 428/195.1
2009/0105361 A1* 4/2009 Ikemura et al. ................ 522/47

FOREIGN PATENT DOCUMENTS

JP          2005-112854           4/2005
WO     WO 2008139226 A1 *  11/2008

* cited by examiner

MIXABLE AND COLOR TONE FREELY REPRODUCIBLE DENTAL COLORING MATERIAL COMPOSITION, AND SET AND METHOD THEREOF

BACKGROUND OF THE INVENTION

1. Field of the Invention

The present invention relates to a dental composition, preferably a paste type dental composition, and more particularly to a dental composition, preferably a paste type dental composition which is mixable and is also capable of freely reproducing a color tone, and a set thereof. The dental composition is used for all kinds of dental materials (for example, fillers, temporary crowns, dental prostheses, implant upper structures, facing crowns and the like) produced from various materials (for example, composite materials, resins, ceramics and the like) which can be used in the dental field. The dental composition can also be directly applied to natural teeth.

2. Description of the Related Art

In current dental treatments, esthetic qualities are one of the most important elements and a dental material is strongly required to have properties so that a prosthesis has a color tone which resembles that of a natural tooth, and also has a beautiful white color.

In order to satisfy aesthetic elements in dental treatments, a dental crown color is reproduced by certain methods using ceramics and resin materials instead of metals. Of these materials, there have been remarkable developments in resin materials and materials having satisfactory abrasion resistance, bending strength, water resistance and the like have recently been proposed. A color sample (shade guide) is usually used with these ceramics and resin materials so as to match the color tone with that of a natural tooth and, therefore, a preliminarily colored material is provided in order to reproduce the color tone of the shade guide.

However, the natural tooth does not always have a single color tone and the color tone varies with a specific site. For example, the teeth of persons who smoke show color tones such as greenish brown color, reddish brown color, yellowish brown color and the like due to nicotine coloration, while a reddish purple or bluish purple pattern may appear on teeth influenced by tetracycline-based drugs. Also, overall color unevenness may be caused by disequilibrium of dental growth processes. In such a case, there is a limitation on the color tone reproduction only using a shade guide and a resin material having a basic color tone.

For the purpose of expressing higher esthetic qualities and the same color tone as that of a natural tooth, a material for partial coloration (stain material) has been proposed as a material having a color tone which is not possessed by the shade guide. The stain material generally is adjusted to various color tones such as brown color and purple color in order to reproduce a partial coloration of the tooth described above, and is also in the form of a liquid or a paste having a low viscosity so as to facilitate partial application to a prosthesis. Some stain materials have pure color tones such as red color, blue color, orange color and the like and are mainly used in combination with other color tones rather than used alone.

Surgical operators such as dentists, dental technicians and the like perform adjustment of the color tone of a dental crown prosthesis using a stain material having a color tone which has been adjusted preliminarily. When a color other than the color tone which has been adjusted preliminarily by a manufacturer is required, plural color tones are mixed. However, the stain material having a preliminarily adjusted color tone contains plural coloring materials (pigments, dyes) which have already been blended, and a more complicated color development structure is imparted by mixing these materials, and thus it is difficult to obtain the color tone desired by the surgical operator. In stain materials having pure colors such as red color, blue color, and orange color of conventional products, there was a limitation on the desired color mixture of the surgical operators in view of chromatology and subtractive color mixture.

Referring to a theory of color, the so-called three primary colors are classified into two kinds, which are the three additive primary colors and the three subtractive primary colors. In the case of the color tone of light, additive primary colors due to three colors of red, blue and green colors are established. The color tones using pigments or dyes such as those used in printing techniques are subtractive primary colors due to three colors of cyan, magenta and yellow colors.

It is theoretically possible to express all color tones by mixing the three subtractive primary colors of cyan, magenta and yellow colors in any concentration on a white-colored base. However, in current printing techniques, complete black may not be obtained even by mixing existing colored materials of cyan, magenta and yellow colors, in many cases. Therefore, in addition to the three subtractive primary colors, a black coloring material is used practically and is generally called CMYK (Cyan, Magenta, Yellow, Key plate). In case coloration on a white-colored base cannot be performed when the color tone is expressed by three subtractive primary colors, it becomes necessary to further use a white colored coloring material.

As a color expressing method, an expression method using a color sample provided by a manufacturer has mainly been used over a long time in the dental field. However, a L*a*b* color system, which is often used in the industrial field, has recently been used in combination. However it has been suggested that complete agreement with human sense of color is not achieved by the L*a*b* color system. A theory advocating the utility of a Munsell color system is disclosed in "Color for Dentistry, Method for Expression of Dental Crown using Munsell Color System" (written by Ikuemon Katayama, published by Japan Academy of Color for Dentistry, 2005, December, Vol. 11, No. 1, P. 39-44). This document describes that evaluation by the Munsell color system agrees with a human evaluation with respect to a dental crown material.

Here, a color expression system as a method of expressing a color tone will be described. Also in the present invention, the invention is explained using two kinds of color systems. First, a L*a*b* color system is defined by CIE (Commission internationale de l'éclairage) and a color is expressed by a lightness index L* and a perceptive chromaticity index a* and b*. This L*a*b* color system is widely used as a uniform perceptual color space in the industrial field. In contrast, a Munsell color system is an expression method by a sensation when a color chip is visually observed, a so-called perceived color. The color is expressed by systematically classifying various colors and defining a scale graduation with respect to each attribute of a color value (symbol V), chromaticness (symbol C) and hue (symbol H). Specifically, the value of color (V) is expressed by the numerical value of 0 to 10 and with respect to the chromaticness, different scale graduation is defined every hue. The hue is expressed by arranging 10 hues of basic hue, red (R), yellow (Y), green (G), blue (B), purple (P), and complementary colors of these basic hues, such as bluish green (BG), bluish purple (BP), reddish purple (RP), yellowish red (YR) and yellowish green (GY) on a 360 degree circumference.

As described above, recent demands for color tone expression have rapidly increased in the dental field, and it has become necessary to develop a dental material which responds to such demand.

JP-A No. 2004-203865 discloses a dental coating material comprising (A) a matrix resin, (B) a filler mixture, (C) one or more kinds of polymerization initiators, and (D) a trace amount of one or more kinds of dental pigments. The invention relates to a coating material which can be used by a brush and is used to adjust a color tone of an artificial tooth.

JP-A No. 2005-112854 discloses a method for correcting a color of a surface of dental prostheses or teeth by applying a photocurable correcting color for a dental basic color. The invention relates to the technique in which correcting colors of orange, blue, white and black colors are used so as to adjust a basic color which is widely used in the dental field. However, application to a peculiar color tone of a specific site of teeth is not possible and definition of the correcting color is chromatologically unclear. Thus it is considered to be impossible to cope with various color tones required for the dental prostheses.

"The Journal of the Japan Dental Technicians' Association, New Placement Technique of Photopolymerizable Rigid Resin" (written by Yasuo Onodera, published by The Japan Dental Technicians' Association (Incorporated), issued on 2006, November, Page. 33-40) describes reproduction of a color of a tooth using an internal stain. However, the method is a method in accordance with the shade guide and had a problem that it is impossible to perform entire color tone reproduction.

SUMMARY OF THE INVENTION

The present inventors have intensively studied about a dental composition, which is mixable, preferably is a paste type and is capable of freely reproducing a color tone, and found out that it is possible to freely reproduce a color tone by using, as a basic color, three colors, particularly three colors in a specific range expressed by a Munsell color system of a dental coloring material composition comprising:
(a) a polymerizable monomer and/or an oligomer,
(b) a polymerization catalyst, and
(c) a pigment and/or a dye, wherein
 a color tone thereof is a cyan, magenta or yellow color based on three subtractive primary colors, and optionally using a dental coloring material composition of white, black and transparent colors in combination as appropriate. Thus, the present invention has been completed.

Accordingly, the present invention provides:
[1] A dental coloring material composition comprising:
(a) a polymerizable monomer and/or an oligomer,
(b) a polymerization catalyst, and
(c) a pigment and/or a dye, wherein
 a color tone thereof is a cyan color based on three subtractive primary colors;
[2] A dental coloring material composition comprising:
(a) a polymerizable monomer and/or an oligomer,
(b) a polymerization catalyst, and
(c) a pigment and/or a dye, wherein
 a color tone thereof is a magenta color based on three subtractive primary colors;
[3] A dental coloring material composition comprising:
(a) a polymerizable monomer and/or an oligomer,
(b) a polymerization catalyst, and
(c) a pigment and/or a dye, wherein
 a color thereof is a yellow color based on three subtractive primary colors;
[4] The dental coloring material composition according to [1], wherein, when the cyan color is tone-evaluated by a Munsell color system, measured values at a white back of a specimen having a thickness of 0.1 mm are as follows: hue (H) of 5PB to 1PB, 10B to 1B, 10GB to 5GB, value of color (V) of 2 to 9, and chromaticness (C) of 6 to 15;
[5] The dental coloring material composition according to [2], wherein, when the magenta color is tone-evaluated by a Munsell color system, measured values at a white back of a specimen having a thickness of 0.1 mm are as follows: hue (H) of 1R, 10RP to 1RP, 10P to 5P, value of color (V) of 2 to 9, and chromaticness (C) of 6 to 17;
[6] The dental coloring material composition according to [3], wherein, when the yellow color is tone-evaluated by a Munsell color system, measured values at a white back of a specimen having a thickness of 0.1 mm are as follows: hue (H) of 1Y to 10Y, 1GY to 2GY, value of color (V) of 4 to 10, and chromaticness (C) of 7 to 17;
[7] The dental coloring material composition according to [1] or [4], which contains, as the pigment and/or the dye of the cyan color, at least one kind selected from among Green No. 3 (Fast Green FCF), Blue No. 1 (Brilliant Blue FCF), Blue No. 2 (Indigo Carmine), Blue No. 201 (Indigo), Blue No. 202 (Patent Blue NA), Blue No. 203 (Patent Blue CA), Blue No. 204 (Carbanthrene Blue), Blue No. 205 (Alphazurine FG), Phthalocyanine Blue, Aluminum Phthalocyanine Blue and Indanthrene Blue;
[8] The dental coloring material composition according to [2] or [5], which contains, as the pigment and/or the dye of the magenta color, at least one kind selected from among Red No. 2 (Amaranth), Red No. 104 (Phloxine), Red No. 105 (Rose Bengal), Red No. 106 (Acid Red), Red No. 201 (Lithol Rubine B), Red No. 202 (Lithol Rubine BCA), Red No. 203 (Lake Red C), Red No. 204 (Lake Red CBA), Red No. 205 (Lithol Red), Red No. 206 (Lithol Red CA), Red No. 207 (Lithol Red BA), Red No. 208 (Lithol Red SR), Red No. 213 (Rhodamine B), Red No. 214 (Rhodamine B Acetate), Red No. 215 (Rhodamine B Stearate), Red No. 218 (Tetrachlorotetrabromofluorescein), Red No. 219 (Brilliant Lake Red R), Red No. 220 (Deep Maroon), Red No. 221 (Toluidine Red), Red No. 223 (Tetrabromofluorescein), Red No. 225 (Sudan III), Red No. 226 (Helindone Pink CN), Red No. 227 (Fast Acid Magenta), Red No. 228 (Permaton Red), Red No. 230(1) (Eosin YS), Red No. 230(2) (Eosin YSK), Red No. 231 (Phloxine BK), Red No. 232 (Rose Bengal K), Red No. 401 (Violamine R), Red No. 404 (Brilliant Fast Scarlet), Red No. 405 (Parmanent Red F5R), Red No. 501 (Medical Scarlet), Red No. 502 (Ponceau 3R), Red No. 503 (Ponceau R), Red No. 504 (Ponceau SX), Red No. 505 (Oil Red XO), Red No. 506 (Fast Red S), Purple No. 201 (Alizurine Purple Lake SS), Purple No. 401 (Alizurol Purple), Naphthol AS (Naphthol Rubine, Naphthol Red FGR, Naphthol Carmine FBB, Naphthol Carmine F3B, Naphthol Red F5RK, Naphthol Red HF4B), BONA Lake (BONA Barium Lake, BONA Calcium Lake, BONA Strontium Lake, BONA Manganese Lake, BONA Magnesium Lake), Lithol Rubine (Brilliant Carmine 6B), Diaminoanthraquinonyl Red, DPP Red BO, Diketopyrolopyrrole, Perylene Red BL, Imidazolone Red HFT, Imidazolone Carmine HF3C, Benzimidazolone Carmine HF4C, Diaminoanthraquinonyl Red, Dichloroquinacridone Magenta, Quinacridone Magenta, Quinacridone Red, Quinacridone Violet, Dioxane Violet and Condensed Azo Scarlet;

[9] The dental coloring material composition according to [3] or [6], which contains, as the pigment and/or the dye of the yellow color, at least one kind selected from among Yellow No. 4 (Tartrazine), Yellow No. 201 (Fluorescein), Yellow No. 202(1) (Uranine), Yellow No. 202(2) (Uranine K), Yellow No. 203 (Quinoline Yellow WS), Yellow No. 204 (Quinoline Yellow SS), Yellow No. 205 (Benzidine Yellow G), Yellow No. 401 (Hanza Yellow), Yellow No. 402 (Pola Yellow 5G), Yellow No. 403(1) (Naphthol Yellow S), Yellow No. 406 (Metanyl Yellow), Yellow No. 407 (Fast Light Yellow 3G), Hanza Yellow 10G, Disazo Yellow (AAMX, AAOT, HR, 4G, 3A, GR, G), Benzimidazolone Yellow (H2G, HG), Isoindoline Yellow (G, R), Pyrazolone Yellow HGR and Diarylide Yellow AAOA;

[10] A dental coloring material set comprising a combination of the composition as defined in [1], [4] or [7], the composition as defined in [2], [5] or [8], and the composition as defined in [3], [6] or [9].

[11] A dental coloring material set comprising: the dental coloring material set as defined in [10], and a white-colored composition comprising:
(a) a polymerizable monomer and/or an oligomer,
(b) a polymerization catalyst, and
(c) a pigment and/or a dye;

[12] A dental coloring material set comprising: the dental color material set as defined in [10], and a black-colored composition comprising:
(a) a polymerizable monomer and/or an oligomer,
(b) a polymerization catalyst, and
(c) a pigment and/or a dye;

[13] A dental coloring material set comprising: the dental color material set as defined in [10],
(1) a white-colored composition comprising:
(a) a polymerizable monomer and/or an oligomer,
(b) a polymerization catalyst, and
(c) a pigment and/or a dye, and
(2) a black-colored composition comprising:
(a) a polymerizable monomer and/or an oligomer,
(b) a polymerization catalyst, and
(c) a pigment and/or a dye;

[14] The dental coloring material set as defined in any one of [10] to [13], which further contains a transparent composition comprising:
(a) a polymerizable monomer and/or an oligomer, and
(b) a polymerization catalyst;

[15] A method for applying the dental coloring material set as defined in any one of [10] to [14], which comprises mixing constituent compositions of each set as defined in any one of [10] to [14] to prepare any color tone composition, and applying the composition to a dental material as a dental coloring material;

[16] The dental coloring material composition as defined in any one of [1] to [9], wherein a paste has a viscosity of 1 to 20 Pa·S as measured in a cone plate-plate system at a frequency sweep of 7 to 1 Hz, an initiation stress of 1.00E+1 Pa and a temperature of 23° C.;

[17] The dental coloring material set as defined in any one of [10] to [14], wherein a paste has a viscosity of 1 to 20 Pa·S as measured in a cone plate-plate system at a frequency sweep of 7 to 1 Hz, an initiation stress of 1.00E+1 Pa and a temperature of 23° C.;

[18] The method according to [15], wherein a paste has a viscosity of 1 to 20 Pa·S as measured in a cone plate-plate system at a frequency sweep of 7 to 1 Hz, an initiation stress of 1.00E+1 Pa and a temperature of 23° C.;

[19] The dental coloring material composition according to any one of [1] to [9], wherein the composition further contains a filler (d) having a particle diameter of 0.001 to 0.1 μm, and a paste has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz;

[20] The dental coloring material set according to any one of [10] to [14], wherein the set further contains a filler (d) having a particle diameter of 0.001 to 0.1 μm, and a paste has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz; and

[21] The method according to [15], wherein the set further contains a filler (d) having a particle diameter of 0.001 to 0.1 μm, and a paste has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

According to the present invention, there is provided a dental composition, preferably of a paste type, which is mixable and is capable of freely reproducing a color tone.

DETAILED DESCRIPTION OF THE INVENTION

Figure 1:
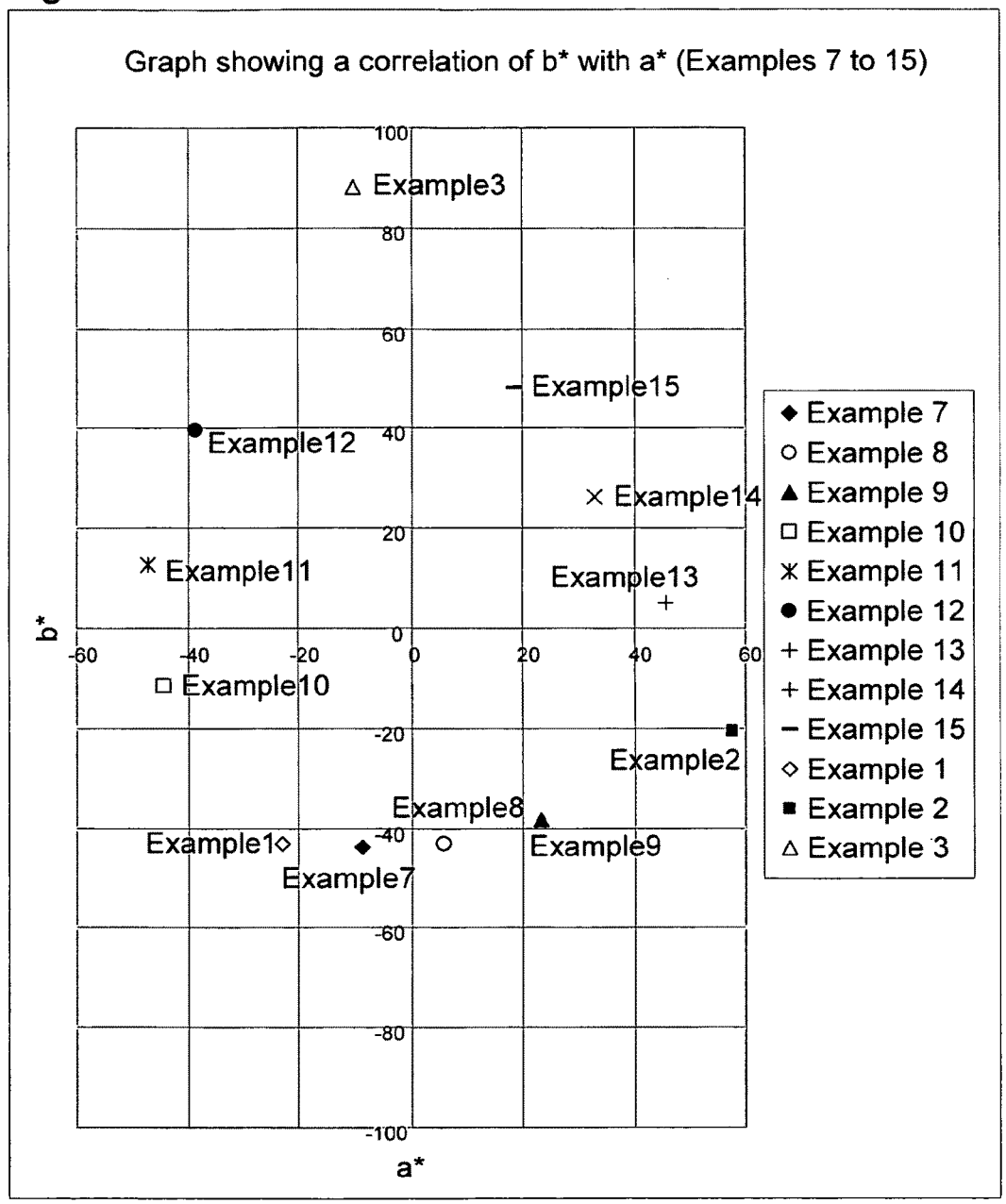
FIG. 1 is a graph showing a correlation of b* with a* of a L*a*b* color system obtained by mixing dental compositions of Examples 1 to 6 and Comparative Examples 1 to 6 and confirming the ease of mixing and color tone reproducibility.

The present invention will be described in detail below.

As for (a) the polymerizable monomer and/or oligomer in the present invention, known polymerizable monomers and/or oligomers can be used without any limitation. Examples of the compounds include monofunctional compounds, for example, (meth)acrylate esters such as methyl (meth)acrylate, ethyl(meth)acrylate, normal-butyl (meth)acrylate, isobutyl(meth)acrylate, tert-butyl (meth)acrylate, pentyl (meth)acrylate, isopentyl (meth)acrylate, neopentyl(meth)acrylate, glycidyl (meth)acrylate, tetrahydrofurfuryl(meth)acrylate, 2-hydroxyethyl(meth)acrylate, 2-hydroxypropyl (meth)acrylate, 3-chloro-2-hydroxypropyl(meth)acrylate, ethylene glycol acetoacetate(meth)acrylate, ethylene glycol mono(meth)acrylate, diethylene glycol mono(meth)acrylate, triethylene glycol mono(meth)acrylate, polyethylene glycol mono(meth)acrylate, methoxydiethylene glycol mono(meth)acrylate, methoxytetraethylene glycol (meth)acrylate, methoxypolyethylene glycol(meth)acrylate, β-(meth)acryloxyethylhydrogen phthalate, β-(meth)acryloxyethylhydrogen succinate, nonylphenoxyethyl (meth)acrylate, phenoxyethyl (meth)acrylate, phenoxydiethylene(meth)acrylate, N-(2-hydroxy-3-(meth)acryloyloxypropyl)-N-phenylglycine, N-(meth)acryloylglycine, 4-(meth)acryloyloxyethyltrimellitic anhydride and the like; vinyl esters such as vinyl acetate, vinyl propionate and the like; vinylethers such as methyl vinyl ether, ethyl vinyl ether, isobutyl vinyl ether, (meth)acrylaldehyde ethyl acetal and the like; alkenylbenzenes such as styrene, vinyltoluene, α-methylstyrene, chlorostyrene and the like; vinyl cyanides such as acrylonitrile, (meth)acrylonitrile and the like; (meth)acrylaldehydes such as (meth)acrylaldehyde, 3-cyano(meth)acrylaldehyde and the like; (meth)acrylic acid amides such as (meth)acrylamide, N-succin (meth)acrylamide, N,N-dimethyl(meth)acrylamide and the like; (meth)acrylic acids or metal salts thereof, such as (meth)acrylic acid, vinylacetic acid, crotonic acid and the like; polymerizable monomers having a phosphate ester group or metal salts thereof, such as acid phosphoethyl(meth)acrylate, acid phosphopropyl(meth)acrylate, 2-(meth)acryloyloxyethylphenylphosphoric acid and the like; polymerizable monomers having a sulfonic acid group or metal salts thereof, such as allylsulfonic acid, (meth)acrylsulfonic acid, styrenesulfonic acid, tert-butyl(meth)acrylamidesulfonic acid and the like, and metal salts thereof.

Examples of difunctional polymerizable monomers include di(meth)acrylates such as ethylenediol, propylenediol, propanediol, butanediol, hexanediol, octanediol, nonanediol, decanediol, eicosanediol and the like; ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butylene glycol di(meth)acrylate and neopentyl glycol di(meth)acrylate; urethane-based polymerizable monomers derived from adducts of vinyl monomers having a hydroxyl group, such as 2-hydroxyethyl(meth)acrylate, 2-hydroxypropyl(meth)acrylate and 3-chloro-2-hydroxypropyl(meth)acrylate, and diisocyanate compounds such as hexamethylene diisocyanate, trimethylhexamethylene diisocyanate, diisocyanatemethylcyclohexane, isophorone diisocyanate and methylbis(4-cyclohexyl isocyanate); (meth)acrylate-based polymerizable monomers having an aromatic ring and an urethane bond derived from adducts of vinyl monomers having a hydroxyl group, such as 2-hydroxyethyl(meth)acrylate, 2-hydroxypropyl(meth)acrylate and 3-chloro-2-hydroxypropyl(meth)acrylate, and aromatic-containing diisocyanate compounds such as diisocyanatemethylbenzene and 4,4'-diphenylmethanediisocyanate; (meth)acrylate-based polymerizable monomers having an aromatic ring and an ether bond, such as 2,2-bis((meth)acryloxyphenyl)propane, 2,2-bis[4-(3-(meth)acryloxy)-2-hydroxypropoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypolyethoxyphenyl)propane, 2,2-bis(4-(meth)acryloxydipropoxyphenyl)propane, 2-(4-(meth)acryloxyethoxyphenyl)-2-(4-(meth)acryloxyphenyl)propane, 2-(4-(meth)acryloxydiethoxyphenyl)-2-(4-(meth)acryloxytriethoxyphenyl)propane, 2-(4-(meth)acryloxydipropoxyphenyl)-2-(4-(meth)acryloxytriethoxyphenyl)propane, 2,2-bis(4-(meth)acryloxyisopropoxyphenyl)propane and the like, 1:2 reaction product of bisphenol A or hydogenated bisphenol A and glycidyl(meth)acrylate, for example, 1:2 adducts of bisphenol A or hydogenated bisphenol A and (meth)acrylate having an epoxy group, such as bisphenol A diglycidylether(meth)acrylic acid adduct.

Examples of the polyfunctional compound having three or more polymerizable functional groups include trimethylolmethane tri(meth)acrylate, trimethylolethane tri(meth)acrylate, trimethylolpropane tri(meth)acrylate, pentaerythritol tetra(meth)acrylate, tri(meth)acrylate having a phosphazene skeleton, tri(meth)acrylate having an isocyanuric acid skeleton, pentaerythritol tetra(meth)acrylate, ditrimethylolpropane tetra(meth)acrylate, urethane-based polymerizable monomers derived from a diisocyanate compound such as diisocyanatemethylbenzene, 4,4'-diphenylmethane diisocyanate, hexamethylene diisocyanate, trimethylhexamethylene diisocyanate, diisocyanatemethylcyclohexane, isophorone diisocyanate or methylbis(4-cyclohexyl isocyanate), and a vinyl monomer having a hydroxyl group, such as glycidol di(meth)acrylate, polymerizable monomers having five or more ethylenically unsaturated groups, such as dipentaerythritolhydroxy penta(meth)acrylate, polymerizable polyfunctional acrylates including polyethylenically unsaturated carbamoyl isocyanurate; polymerizable polyfunctional acrylates having an urethane bond, such as phenyl glycidyl ether acrylate hexamethylene diisocyanate urethane prepolymer, phenylglycidylethertoluenediisocyanate urethane prepolymer, pentaerythritol triacrylate toluene diisocyanate urethane prepolymer and pentaerythritol triacrylate isophorone diisocyanate urethane prepolymer; ditrimethylolpropane tetraacrylate, ethoxylated pentaerythritol tetraacrylate, propoxylated pentaerythritol tetraacrylate, pentaerythritol tetra (meth)acrylate, dipentaerythritol tetra(meth)acrylate, dipentaerythritol penta(meth)acrylate, dipentaerythritol hexa (meth)acrylate, trimethylpropane tri(meth)acrylate and the like.

As for (b) the polymerization catalyst compound in the dental composition of the present invention, for example, known polymerization catalysts are used without any limitation. Examples of the photopolymerization catalyst include benzophenone, diacetil, benzil, 4,4'-dimethoxybenzil, 4,4'-dimethoxybenzil, 4,4'-oxybenzil, 4,4'-chlorobenzil, camphorquinone, camphorquinonecarboxylic acid, 2,3-pentadion, 2,3-octadion, 9,10-phenanthrenequinone, acenaphthenequinone, 2,4,6-trimethylbenzoyldiphenylphosphine oxide, 2,6-dimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, methyl 2,4,6-trimethylbenzoylphenylphosphinate, ethyl 2,4,6-trimethylbenzoylphenylphosphinate, phenyl 2,4,6-trimethylbenzoylphenylphosphinate and the like. As for the chemical polymerization catalyst compound, for example, diacyl peroxides, peroxyesters, dialkyl peroxides, peroxyketals, ketone peroxides, hydroperoxides and the like are effective. Specific examples of diacyl peroxides include benzoyl peroxide, 2,4-dichlorobenzoyl peroxide, m-toluoyl peroxide and the like.

As for the promotor of the polymerization initiator, for example, known promotors are used without any limitation, and examples thereof include N,N-dimethylaniline, N,N-diethylaniline, N,N-dibenzylaniline, N,N-dimethyl-p-toluidine, N,N-diethyl-p-toluidine, N,N-dihydroxyethyl-p-toluidine, N,N-dimethylbenzoic acid, N,N-diethylbenzoic acid, ethyl N,N-dimethylbenzoate, ethyl N,N-diethylbenzoate, methyl N,N-dimethylbenzoate, methyl N,N-diethylbenzoate, N,N-dimethylaminobenzaldehyde, N,N-dihydroxyethylaniline, p-dimethylaminophenethyl alcohol, N,N-dimethylaminoethyl methacrylate, N,N-dimethylaminoethyl methacrylate, triethylamine, tributylamine, tripropylamine, N-ethylethanolamine and the like.

In the cyan-colored composition of the present invention, when the color is tone-evaluated by a Munsell color system, measured values at a white back of a specimen having a thickness of 0.1 mm are preferably as follows: hue (H) of 5PB to 1PB, 10B to 1B, 10GB to 5GB, value of color (V) of 2 to 9, and chromaticness (C) of 6 to 15; more preferably as follows: (H) of 3PB to 1PB, 10B to 1B, 10GB to 8GB, (V) of 3 to 8, and (C) of 7 to 14; and still more preferably as follows: (H) of 1PB, 10B to 1B, (V) of 4 to 7, and (C) of 8 to 13.

In the cyan-colored composition of the present invention, when the color is tone-evaluated by a L*a*b* color system, measured values at a white back of a specimen having a thickness of 0.1 mm are preferably as follows: $30 \leq L^* \leq 100$, $a^* \leq 0$ and $-10 \leq b^* \leq -100$, and more preferably as follows: $1/2 a^* \geq b^*$.

Examples of the pigment and/or the dye used for cyan color development in the present invention are as follows:

Green No. 3 (Fast Green FCF), Blue No. 1 (Brilliant Blue FCF), Blue No. 2 (Indigo Carmine), Blue No. 201 (Indigo), Blue No. 202 (Patent Blue NA), Blue No. 203 (Patent Blue CA), Blue No. 204 (Carbanthrene Blue), Blue No. 205 (Alphazurine FG), Phthalocyanine Blue, Aluminum Phthalocyanine Blue and Indanthrene Blue. Of these, Phthalocyanine Blue and Aluminum Phthalocyanine Blue are preferably used. As for Phthalocyanine Blue, for example, Pigment Blue 15, Pigment Blue 15:1, Pigment Blue 15:2, Pigment Blue 15:3, Pigment Blue 15:4, Pigment Blue 15:5 and Pigment Blue 15:6 are particularly preferred. As for Aluminum Phthalocyanine Blue, for example, Pigment Blue 79 is particularly preferred.

In the magenta-colored composition of the present invention, when the color is tone-evaluated by a Munsell color system, measured values at a white back of a specimen having a thickness of 0.1 mm are preferably as follows: hue (H) of 1R, 10RP to 1RP, 10P to 5P, value of color (V) of 2 to 9, and chromaticness (C) of 6 to 17; more preferably as follows: (H) of 10RP to 1RP, 10P to 8P, (V) of 3 to 8, and (C) of 7 to 16; and still more preferably as follows: (H) of 8RP to 1RP, 10P, (V) of 4 to 7, and (C) of 8 to 15.

In the magenta-colored composition of the present invention, when the color is tone-evaluated by a L*a*b* color system, measured values at a white back of a specimen having a thickness of 0.1 mm are preferably as follows: $30 \leq L^* \leq 100$, $10 \leq a^* \leq 100$ and $10 \leq b^* \leq -100$.

Examples of the pigment and/or the dye used for magenta color development in the present invention are as follows:

Red No. 2 (Amaranth), Red No. 104 (Phloxine), Red No. 105 (Rose Bengal), Red No. 106 (Acid Red), Red No. 201 (Lithol Rubine B), Red No. 202 (Lithol Rubine BCA), Red No. 203 (Lake Red C), Red No. 204 (Lake Red CBA), Red No. 205 (Lithol Red), Red No. 206 (Lithol Red CA), Red No. 207 (Lithol Red BA), Red No. 208 (Lithol Red SR), Red No. 213 (Rhodamine B), Red No. 214 (Rhodamine B Acetate), Red No. 215 (Rhodamine B Stearate), Red No. 218 (Tetrachlorotetrabromofluorescein), Red No. 219 (Brilliant Lake Red R), Red No. 220 (Deep Maroon), Red No. 221 (Toluidine Red), Red No. 223 (Tetrabromofluorescein), Red No. 225 (Sudan III), Red No. 226 (Helindone Pink CN), Red No. 227 (Fast Acid Magenta), Red No. 228 (Permaton Red), Red No. 230(1) (Eosin YS), Red No. 230(2) (Eosin YSK), Red No. 231 (Phloxine BK), Red No. 232 (Rose Bengal K), Red No. 401 (Violamine R), Red No. 404 (Brilliant Fast Scarlet), Red No. 405 (Parmanent Red F5R), Red No. 501 (Medical Scarlet), red color 502 (Ponceau 3R), Red No. 503 (Ponceau R), Red No. 504 (Ponceau SX), Red No. 505 (Oil Red XO), Red No. 506 (Fast Red S), Purple No. 201 (Alizurine Purple Lake SS), Purple No. 401 (Alizurol Purple), Naphthol AS (Naphthol Rubine, Naphthol Red FGR, Naphthol Carmine FBB, Naphthol Carmine F3B, Naphthol Red F5RK, Naphthol Red HF4B), BONA Lake (BONA Barium Lake, BONA Calcium Lake, BONA Strontium Lake, BONA Manganese Lake, BONA Magnesium Lake), Lithol Rubine (Brilliant Carmine 6B), Diaminoanthraquinonyl Red, DPP Red BO, Diketopyrolopyrrole, Perylene Red BL, Imidazolone Red HFT, Imidazolone Carmine HF3C, Benzimidazolone Carmine HF4C, Diaminoanthraquinonyl Red, Dichloroquinacridone Magenta, Quinacridone Magenta, Quinacridone Red, Quinacridone Violet, Dioxane Violet and Condensed Azo Scarlet.

Of these, for example, Lithol Rubine, Naphthol Carmine FBB, Naphthol Rubine F6B, Quinacridone Magenta, Quinacridone Scarlet, Diketopyrolopyrrole, Dioxane Violet, Quinacridone Red and Quinacridone Violet are preferably used. As for Lithol Rubine, Pigment Red 57:1 is particularly preferred. As for Naphthol Carmine FBB, Pigment Red 146 is particularly preferred. As for Naphthol Rubine F6B, Pigment Red 184 is particularly preferred. As for Quinacridone Magenta, Pigment Red 122 and Pigment Red 202 are particularly preferred. As for Quinacridone Scarlet, Pigment Red 209 is particularly preferred. As for Diketopyrolopyrrole, Pigment Red 264 is particularly preferred. As for Dioxane Violet, Pigment Violet 23 and Pigment Violet 37 are particularly preferred. As for Quinacridone Red, Pigment Violet 19γ is particularly preferred. As for Quinacridone Violet, Pigment Violet 19β is particularly preferred.

In the yellow-colored composition of the present invention, when the color is tone-evaluated by a Munsell color system, measured values at a white back of a specimen having a thickness of 0.1 mm are preferably as follows: hue (H) of 1Y to 10Y, 1GY to 2GY, value of color (V) of 4 to 10, and chromaticness (C) of 7 to 17; more preferably as follows: (H) of 2Y to 10Y, (V) of 5 to 10, and (C) of 8 to 16; and still more preferably as follows: (H) of 3Y to 9Y, (V) of 6 to 10, and (C) of 9 to 15.

In the yellow-colored composition of the present invention, when the color is tone-evaluated by a L*a*b* color system, measured values at a white back of a specimen having a thickness of 0.1 mm are preferably as follows: $50 \leq L^* \leq 100$, $-50 \leq a^* \leq 50$ and $20 \leq b^* \leq 100$. It is preferred that $-a^* + 20 \leq b^*$ when $a^* \leq 0$, and $a^* + 20 \leq b^*$ when $a^* \geq 0$.

Examples of the pigment and/or the dye used for yellow color development in the present invention are as follows:

Yellow No. 4 (Tartrazine), Yellow No. 201 (Fluorescein), Yellow No. 202(1) (Uranine), Yellow No. 202(2) (Uranine K), Yellow No. 203 (Quinoline Yellow WS), Yellow No. 204 (Quinoline Yellow SS), Yellow No. 205 (Benzidine Yellow G), Yellow No. 401 (Hanza Yellow), Yellow No. 402 (Pola Yellow 5G), Yellow No. 403(1) (Naphthol Yellow S), Yellow No. 406 (Metanyl Yellow), Yellow No. 407 (Fast Light Yellow 3G), Hanza Yellow 10G, Disazo Yellow (AAMX, AAOT, HR, 4G, 3A, GR, G), Benzimidazolone Yellow (H2G, HG), Isoindoline Yellow (G, R), Pyrazolone Yellow HGR and Diarylide Yellow AAOA.

Of these, Disazo Yellow, Diarylide Yellow, Benzimidazolone Yellow and Isoindoline Yellow are preferably used. As for Disazo Yellow 3A, Pigment Yellow 12 is particularly preferred. As for Disazo Yellow GR, Pigment Yellow 13 is particularly preferred. As for Disazo Yellow G, Pigment Yellow 14 is particularly preferred. As for Diarylide Yellow AAOA, Pigment Yellow 17 is particularly preferred. As for Benzimidazolone Yellow H2G, Pigment Yellow 120 is particularly preferred. As for Benzimidazolone Yellow HG, Pigment Yellow 180 is particularly preferred. As for Isoindoline Yellow, Pigment Yellow 185 is particularly preferred.

Examples of the pigment and/or the dye used for white color development in the present invention are as follows:

white lead, zinc oxide, titanium oxide, antimony white, zirconium white, calcium carbonate, kaolin clay, barium sulfate, alumina white, talc and white carbon.

Of these, titanium oxide is preferably used.

Examples of the pigment and/or the dye used for black color development in the present invention are as follows:
aniline black, carbon black, graphite black, black iron oxide, anthraquinone black and perylene black.

Of these, carbon black and black iron oxide are preferably used.

It is preferred that the transparent composition of the present invention contains neither pigment nor dye.

Each amount (the total amount when plural pigments and/or dyes are contained) of various pigments and dyes to be blended with cyan-colored, magenta-colored, yellow-colored, white-colored and black-colored compositions of the present invention is preferably from 0.002 to 4 parts by weight, more preferably from 0.01 to 3 parts by weight, and most preferably from 0.02 to 2 parts by weight. When the content of the pigment and dye in the composition is too large, the resulting composition has a dark color. In contrast, when the content is too small, the resulting composition has a light color and it becomes impossible to reproduce theory of color of three subtractive primary colors.

For the purpose of improving dispersibility of the pigment and dye in the composition of the present invention, the composition can also contain 0.002 to 4 parts by weight of barium sulfate ($BaSO_4$).

For the purpose of improving light transmittance, it is preferred that the cyan-colored, magenta-colored and yellow-colored compositions do not contain titanium oxide as the white color pigment.

In the dental coloring material composition of the present invention, a filler can be optionally used. As for the filler, an inorganic substance or an organic substance and a composite are used. Examples of the inorganic filler include soda glass, lithium borosilicate glass, barium glass, strontium glass, zinc glass, fluoroaluminum borosilicate glass, borosilicate glass, crystal quartz, fused silica, synthetic silica, alumina silicate, amorphous silica, glass ceramic or a mixture thereof. There is no particular limitation on a particle size of the inorganic filler and fillers having a particle diameter of several nanometers to several tens of micronmeters are selected. The inorganic filler is preferably subjected to a conventionally known surface treatment. Examples of the surface treating agent include silane compounds such as vinyltrimethoxysilane, vinyltriethoxysilane, vinyltrichlorosilane, vinyltri($\beta$-methoxyethoxy)silane, $\gamma$-methacryloxypropyltrimethoxysilane, $\gamma$-glycidoxypropyltrimethoxysilane, $\gamma$-mercaptopropyltrimethoxysilane, $\gamma$-aminopropyltriethoxysilane and the like. As for the organic filler, a powder (composite filler) of a composite, which is obtained by dispersing an inorganic filler in a polymer powder of the above polymerizable monomer or a polymerizable monomer, followed by polymerization, can be used.

A fluorescent agent can be optionally added. A natural tooth has fluorescence and it is possible to further approximate the color tone to that of the natural tooth by imparting fluorescence to the dental coloring material composition in the present invention. Examples of the fluorescent agent used in the present invention include violanthrone-based compounds, isoviolanthrone-based compounds, perylene-based compounds, thioxanthene-based compounds, coumarin-based compounds, anthraquinone-based compounds, benzopyran-based compounds, naphthalimide-based or naphthalic acid-based compounds, benzopiteridin-based compounds, pyrazine-based compounds, cyanopyrazine-based compounds, stilbene-based compounds, diaminodiphenyl-based compounds, imidazole-based compounds, imidazolone-based compounds, triazole-based compounds, thiazole-based compounds, oxazole-based compounds, carbostyryl-based compounds, naphthalimide-based compounds, pyrazoline-based compounds, dihydropyridine-based compounds and the like.

Furthermore, it is possible to optionally add various additives such as polymerization inhibitors, ultraviolet absorbers and the like, and solvents to the dental coloring material composition in the present invention.

Examples of the polymerization inhibitor include hydroquinone, hydroquinone monomethyl ether, butylated hydroxytoluene and the like. Of these, hydroquinone monomethyl ether and butylated hydroxytoluene are preferred.

Examples of the solvent include water, ethanol, i-propanol, acetone, dimethyl sulfoxide, dimethylformamide, ethyl acetate, butyl acetate and the like.

It becomes possible to perform color mixture of color materials by theory of three subtractive primary colors using cyan-colored, magenta-colored and yellow-colored composition of the present invention in combination. It is also possible to freely adjust the value of color and chromaticness of mixed color materials by using white-colored, black-colored and transparent composition in combination as appropriate. That is, it becomes possible to apply all existing colors expressed by three subtractive primary colors to dental materials by the composition and the method of the present invention.

It is possible to blend (d) a filler having a particle diameter of 0.001 to 0.1 μm so as to adjust the viscosity of the composition of the present invention and to impart proper thixotropic nature.

The amount of (d) the filler is preferably from 0.001 to 100 parts by weight, more preferably from 0.01 to 50 parts by weight, and most preferably from 0.05 to 30 parts by weight.

The composition of the present invention is used for the purpose of being mixed, and therefore, it can be a liquid or powder type, and is preferably a low viscosity paste type. A low viscosity paste composition is operated by a writing brush, a brush, a probe or the like. It is preferred to use a dental coloring material composition having viscosity characteristics suited to the operation, namely, a dental coloring material composition which has a viscosity of 2 to 20 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

EXAMPLES

The present invention will be described in detail by way of Examples and Comparative Examples. The present invention is not limited to these Examples.

Abbreviations of compounds used in Examples of the present invention are as follows.
CQ: dl-camphorquinone
APO: 2,4,6-trimethylbenzoyl-diphenylphosphine oxide
DMBE: Ethyl N,N-dimethylbenzoate
DPH: Dipentaerythritol hexaacrylate
UDMA: Urethane diacrylate
BisGMA: Bisphenol A diglycidyl methacrylate
3G: Triethylene glycol dimethacrylate
NPG: Neopentyl glycol dimethacrylate
TMPT: Trimethylolpropane trimethacrylate
R-8200: AEROSIL R-8200 (manufactured by NIPPON AEROSIL CO., LTD.) (average particle diameter: 0.012 μm)

R-972: AEROSIL R-972 (manufactured by NIPPON AEROSIL CO., LTD.) (average particle diameter: 0.016 μm)
Pigment for cyan color: Phthalocyanine Blue (P.B 15, P.B 15:3)
Pigment for magenta color: Quinacridone Red, Quinacridone Magenta
Pigment for yellow color: Benzimidazolone Yellow HG, Disazo Yellow GR
Pigment for white color: Titanium oxide
Pigment for black color: Black iron oxide
Solidex Stain (manufactured by SHOFU INC.)

The methods for evaluation of the materials used in Examples of the present invention are shown below.

(1) Evaluation of Color Tone of L*a*b* Color System and Munsell Color System

Each of prepared photocurable compositions is collected on a cover glass and is placed on another cover glass via a spacer having a thickness of 0.1 mm. A sample interposed between two cover glasses is pressed from upper and lower directions and, after irradiating a surface and a rear surface with light using a photopolymerization device (Solidilight, manufactured by SHOFU INC.) for each 1 minute, the cover glasses are removed. Colorimetry (L*a*b* color system, Munsell color system) of the specimen thus obtained was carried out using a spectrophotometric calorimeter CM-2002 (manufactured by Konica Minolta Holdings, Inc.).

(2) Judgment of Mixing Property

Colored compositions are collected at each mixing ratio on a mixing pad and then mixed with a spatula. It was visually evaluated how many seconds it takes to obtain a uniform color tone when mixing under given conditions.

Examples and Comparative Examples of the dental composition of the present invention are shown in Table 1. The measurement results are shown in Table 2.

TABLE 1

| | Color | UDMA | 3G | CQ | DMBE | R8200 | Phthalocyanine Blue | Quinacridone Magenta | Benzimidazolone Yellow HG | Titanium oxide | Black iron oxide |
|---|---|---|---|---|---|---|---|---|---|---|---|
| Example 1 | Cyan | 70 | 30 | 0.5 | 1.5 | 9 | 0.75 | — | — | — | — |
| Example 2 | Magenta | 70 | 30 | 0.4 | 2 | 9 | — | 0.75 | — | — | — |
| Example 3 | Yellow | 70 | 30 | 0.6 | 1 | 9 | — | — | 0.75 | — | — |
| Example 4 | White | 70 | 30 | 0.2 | 0.5 | 9 | — | — | — | 2.5 | — |
| Example 5 | Black | 70 | 30 | 1 | 1 | 9 | — | — | — | — | 1.5 |
| Example 6 | Clear | 70 | 30 | 0.2 | 0.5 | 9 | — | — | — | — | — |
| Comparative Example 1 | Blue | (Solidex Stain Blue) (Ultramarine Blue: P.B29 and titanium oxide are used as pigments.) | | | | | | | | | |
| Comparative Example 2 | Red | (Solidex Stain Red) (Condensed Azo Red: P.R144 and titanium oxide are used as pigments.) | | | | | | | | | |
| Comparative Example 3 | Yellow | (Solidex Stain Yellow) (Condensed Azo Yellow GR: P.Y95 and titanium are used as pigments.) | | | | | | | | | |
| Comparative Example 4 | White | (Solidex Stain White) (Titanium oxide is used as a pigment.) | | | | | | | | | |
| Comparative Example 5 | Black | (Solidex Stain Black) (Black ion oxide is used as a pigment.) | | | | | | | | | |
| Comparative Example 6 | Clear | (Solidex Stain Clear) | | | | | | | | | |

All of dental compositions of Example 1 to 6 and Comparative Example 1 to 6 are pasty.

TABLE 2

| | | L*a*b* color system | | | Munsell color system | | |
|---|---|---|---|---|---|---|---|
| | Color | L* | a* | b* | Hue | Value of color | Chromaticness |
| Example 1 | Cyan | 53.8 | −23.2 | −42.6 | 7.1B | 5.3 | 11.7 |
| Example 2 | Magenta | 54.9 | 54.9 | −21.3 | 1.6RP | 5.3 | 13.9 |
| Example 3 | Yellow | 90.0 | −12.3 | 82.5 | 7.7Y | 8.9 | 11.2 |
| Example 4 | White | 96.8 | −1.2 | 0.7 | 2.5G | 9.6 | 0.2 |
| Example 5 | Black | 34.0 | 0.9 | 0.1 | 9.8RP | 3.3 | 0.2 |
| Example 6 | Clear | 96.7 | −0.4 | −0.4 | 8.0B | 9.6 | 0.2 |
| Comparative Example 1 | Blue | 51.3 | 25.6 | −64.1 | 7.2PB | 5.0 | 16.1 |
| Comparative Example 2 | Red | 59.8 | 57.1 | 20.3 | 2.5R | 5.8 | 13.8 |
| Comparative Example 3 | Yellow | 89.8 | −5.5 | 89.1 | 5.0Y | 8.9 | 12.3 |
| Comparative Example 4 | White | 97.0 | −0.8 | 1.1 | 6.6GY | 9.6 | 0.1 |
| Comparative Example 5 | Black | 44.2 | 2.7 | 8.6 | 9.0YR | 4.3 | 1.4 |
| Comparative Example 6 | Clear | 96.8 | −0.4 | −0.2 | 2.1B | 9.6 | 0.1 |

The colors of Examples 1 to 3 are within a range of a color tone based on three subtractive primary colors selected this time. However, the colors of Comparative Examples 1 and 2 deviate from a range of a cyan color (hue (H) of 5PB to 1PB, 10B to 1B, value of color (V) of 2 to 9, chromaticness (C) of 6 to 14) and a magenta color (hue (H) of 1RP, 10P to 8P, value of color (V) of 3 to 8, chromaticness (C) of 7 to 16) based on three subtractive primary colors selected this time.

Figure 2:
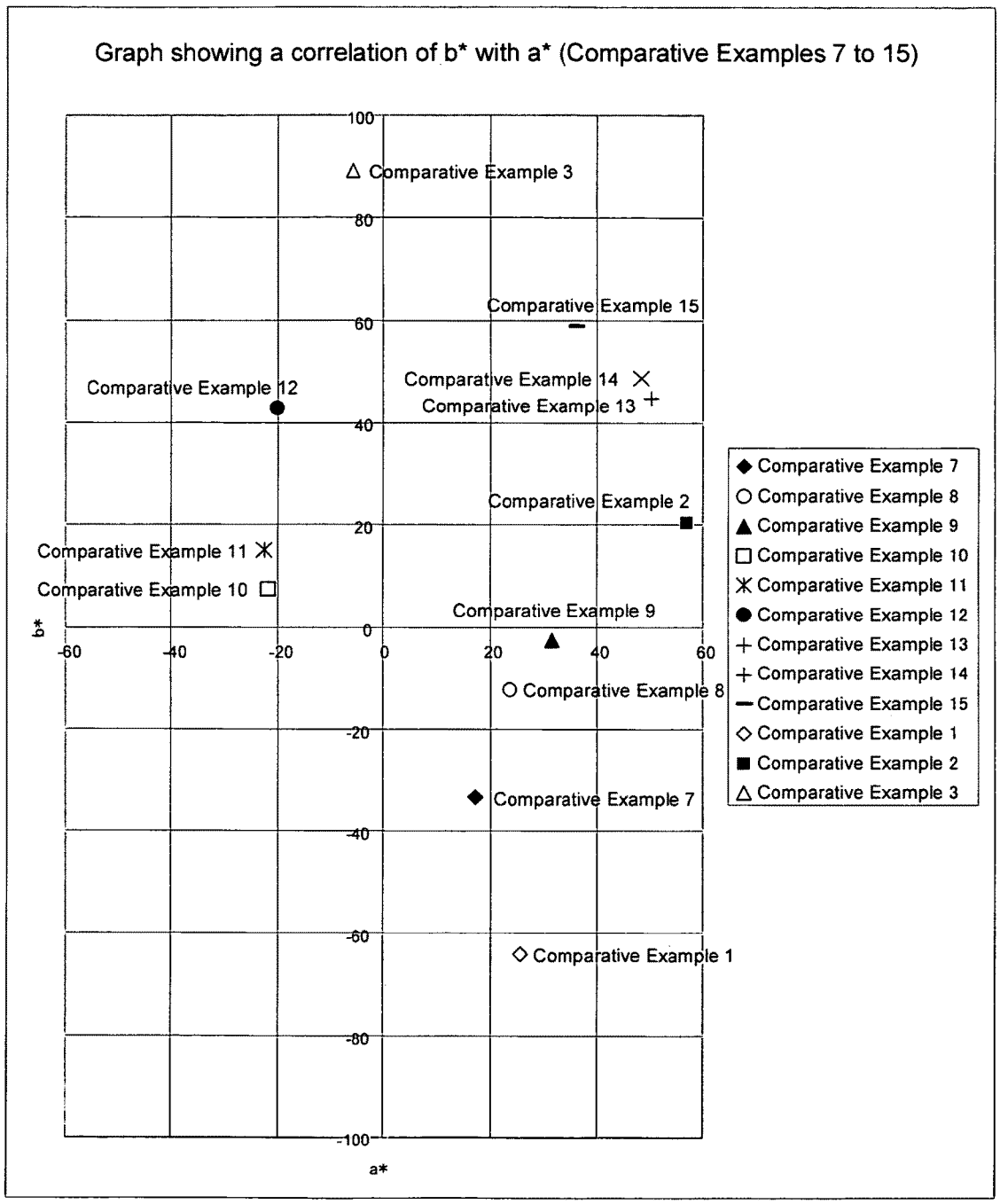
FIG. 2 is a graph showing a correlation of b* with a* of a L*a*b* color system obtained by mixing dental compositions of Examples 1 to 6 and Comparative Examples 1 to 6 and confirming the ease of mixing and color tone reproducibility.

Next, the compositions of Examples 1 to 6 were mixed of the composition of Comparative Examples 1 to 6 and the ease of mixing and color tone reproducibility were confirmed. The measurement data are shown in Table 3, and graphs showing a correlation of b* with a* of a L*a*b* color system are shown in FIGS. 1 and 2.

TABLE 3

| | | Mixing time | L*a*b* color system | | | Munsell color system | | |
|---|---|---|---|---|---|---|---|---|
| | Mixing ratio | (seconds) | L* | a* | b* | H | V | C |
| Example 7 | Example 1:Example 2 = 3:1 | 13 | 47.7 | −8.6 | −43.8 | 1.0PB | 4.6 | 11.0 |
| Example 8 | Example 1:Example 2 = 1:1 | 15 | 43.4 | 5.8 | −43.1 | 5.1PB | 4.2 | 10.5 |
| Example 9 | Example 1:Example 2 = 1:3 | 15 | 45.4 | 23.4 | −38.6 | 9.8PB | 4.4 | 10.2 |
| Example 10 | Example 1:Example 3 = 3:1 | 19 | 52.9 | −44.3 | −11.6 | 6.4BG | 5.1 | 9.4 |
| Example 11 | Example 1:Example 3 = 1:1 | 16 | 59.0 | −47.2 | 12.7 | 6.0G | 5.7 | 9.0 |
| Example 12 | Example 1:Example 3 = 1:3 | 15 | 64.6 | −38.6 | 39.4 | 9.0GY | 6.3 | 8.6 |
| Example 13 | Example 2:Example 3 = 3:1 | 17 | 54.1 | 45.8 | 5.1 | 8.6RP | 5.3 | 10.7 |
| Example 14 | Example 2:Example 3 = 1:1 | 15 | 61.1 | 33.0 | 26.2 | 8.0R | 6.0 | 8.6 |
| Example 15 | Example 2:Example 3 = 1:3 | 14 | 70.2 | 18.4 | 48.1 | 6.7YR | 6.9 | 8.6 |
| Comparative Example 7 | Comparative Example 1:Comparative Example 2 = 3:1 | 55 | 44.7 | 17.3 | −33.4 | 9.1PB | 4.3 | 8.5 |
| Comparative Example 8 | Comparative Example 1:Comparative Example 2 = 1:1 | 52 | 43.7 | 23.7 | −12.3 | 10.0P | 4.2 | 5.9 |
| Comparative Example 9 | Comparative Example 1:Comparative Example 2 = 1:3 | 61 | 45.7 | 31.6 | −2.6 | 5.6RP | 4.4 | 7.1 |
| Comparative Example 10 | Comparative Example 1:Comparative Example 3 = 3:1 | 58 | 52.1 | −21.4 | 7.4 | 5.1G | 5.1 | 4.1 |
| Comparative Example 11 | Comparative Example 1:Comparative Example 3 = 1:1 | 60 | 53.6 | −22.5 | 15.0 | 1.2G | 5.2 | 4.5 |
| Comparative Example 12 | Comparative Example 1:Comparative Example 3 = 1:3 | 53 | 64.5 | −20.0 | 42.9 | 4.2GY | 6.3 | 6.5 |
| Comparative Example 13 | Comparative Example 2:Comparative Example 3 = 3:1 | 55 | 61.1 | 50.4 | 44.8 | 8.4R | 6.0 | 13.3 |
| Comparative Example 14 | Comparative Example 2:Comparative Example 3 = 1:1 | 52 | 62.3 | 48.4 | 48.4 | 9.2R | 6.1 | 13.2 |
| Comparative Example 15 | Comparative Example 2:Comparative Example 3 = 1:3 | 64 | 69.4 | 36.1 | 58.8 | 2.9YR | 6.8 | 12.2 |

As is apparent from Table 2, the mixing time of the compositions of Examples 7 to 15 is from 13 to 19 seconds, whereas, the mixing time of the compositions of Comparative Examples 7 to 15 is from 52 to 64 seconds. Thus, it is found that the compositions of Examples are easily mixed when compared with the compositions of Comparative Examples.

As is apparent from Table 4 and Table 5, the compositions of Examples 1 to 3 and 7 to 15 are aligned at an equal interval and have regularity, whereas the compositions of Comparative Examples 1 to 3 and 7 to 15 have no regularity. Thus, the compositions of the Examples have regularity in mixing and it is easy to reproduce a color tone.

Furthermore, value of color and chromaticness when the compositions of Example 1 to 3 are mixed with the compositions of Examples 4 to 6 are shown in Table 4.

TABLE 4

| | | Mixing time | L*a*b* color system | | | | Munsell color system | | |
|---|---|---|---|---|---|---|---|---|---|
| | Mixing ratio | (seconds) | C* | L* | a* | b* | H | V | C |
| Example 16 | Example 1:Example 4 = 3:1 | 13 | 46.5 | 50.0 | −4.8 | −46.2 | 2.1PB | 4.9 | 11.5 |
| Example 17 | Example 1:Example 4 = 1:1 | 15 | 43.3 | 57.9 | −8.9 | −42.4 | 1.2PB | 5.6 | 10.8 |
| Example 18 | Example 1:Example 4 = 1:3 | 15 | 37.0 | 68.9 | −13.5 | −34.5 | 9.9B | 6.7 | 9.2 |
| Example 19 | Example 2:Example 4 = 3:1 | 19 | 56.5 | 51.7 | 55.5 | −10.4 | 4.1RP | 5.0 | 13.2 |
| Example 20 | Example 2:Example 4 = 1:1 | 16 | 50.7 | 59.5 | 49.0 | −13.2 | 3.0RP | 5.8 | 12.3 |
| Example 21 | Example 2:Example 4 = 1:3 | 15 | 40.8 | 69.4 | 38.5 | −13.6 | 1.6RP | 6.8 | 10.0 |
| Example 22 | Example 3:Example 4 = 3:1 | 17 | 84.0 | 91.4 | −11.2 | 83.3 | 7.1Y | 9.0 | 11.3 |
| Example 23 | Example 3:Example 4 = 1:1 | 15 | 71.4 | 92.8 | −12.0 | 70.4 | 7.8Y | 9.2 | 9.5 |

TABLE 4-continued

| | Mixing ratio | Mixing time (seconds) | L*a*b* color system | | | | Munsell color system | | |
|---|---|---|---|---|---|---|---|---|---|
| | | | C* | L* | a* | b* | H | V | C |
| Example 24 | Example 3:Example 4 = 1:3 | 14 | 53.4 | 94.3 | -12.1 | 52.0 | 9.0Y | 9.3 | 6.8 |
| Example 25 | Example 1:Example 5 = 3:1 | 15 | 30.2 | 42.8 | -18.1 | -24.2 | 5.2B | 4.2 | 6.9 |
| Example 26 | Example 1:Example 5 = 1:1 | 17 | 18.6 | 39.2 | -12.1 | -14.1 | 4.7B | 3.8 | 4.1 |
| Example 27 | Example 1:Example 5 = 1:3 | 21 | 6.7 | 33.1 | -4.2 | -5.1 | 5.6B | 3.2 | 1.4 |
| Example 28 | Example 2:Example 5 = 3:1 | 18 | 35.5 | 41.6 | 32.7 | -14.0 | 1.3RP | 4.0 | 7.9 |
| Example 29 | Example 2:Example 5 = 1:1 | 20 | 18.9 | 36.6 | 17.1 | -7.9 | 0.9RP | 3.6 | 3.8 |
| Example 30 | Example 2:Example 5 = 1:3 | 14 | 8.6 | 36.4 | 7.8 | -3.7 | 0.7RP | 3.5 | 1.6 |
| Example 31 | Example 3:Example 5 = 3:1 | 13 | 42.3 | 60.2 | -5.5 | 41.9 | 7.0Y | 5.9 | 5.7 |
| Example 32 | Example 3:Example 5 = 1:1 | 13 | 32.8 | 54.9 | -3.6 | 32.4 | 6.5Y | 5.4 | 4.8 |
| Example 33 | Example 3:Example 5 = 1:3 | 15 | 23.0 | 49.1 | -2.7 | 22.8 | 6.3Y | 4.8 | 3.1 |
| Example 34 | Example 1:Example 6 = 3:1 | 16 | 45.5 | 64.7 | -29.5 | -34.6 | 5.1B | 6.3 | 10.6 |
| Example 35 | Example 1:Example 6 = 1:1 | 13 | 32.6 | 77.1 | -22.9 | -23.3 | 5.2B | 7.6 | 7.4 |
| Example 36 | Example 1:Example 6 = 1:3 | 17 | 20.4 | 85.0 | -14.7 | -14.1 | 5.6B | 8.4 | 4.5 |
| Example 37 | Example 2:Example 6 = 3:1 | 18 | 49.6 | 62.7 | 45.5 | -19.6 | 0.8RP | 6.1 | 12.0 |
| Example 38 | Example 2:Example 6 = 1:1 | 13 | 38.6 | 72.2 | 34.3 | -17.8 | 9.5P | 7.1 | 9.4 |
| Example 39 | Example 2:Example 6 = 1:3 | 15 | 24.1 | 80.8 | 21.2 | -11.6 | 8.9P | 7.9 | 6.2 |
| Example 40 | Example 3:Example 6 = 3:1 | 14 | 65.2 | 91.1 | -12.9 | 63.9 | 8.7Y | 9.0 | 8.5 |
| Example 41 | Example 3:Example 6 = 1:1 | 19 | 54.8 | 91.3 | -13.4 | 49.4 | 9.0Y | 9.0 | 6.4 |
| Example 42 | Example 3:Example 6 = 1:3 | 14 | 36.8 | 93.3 | -10.1 | 35.4 | 0.1GY | 9.2 | 4.5 |

It is seen from Examples 16 to 24 that the value of color is increased by adding a white color, from Examples 25 to 33 that the value of color is decreased by adding a black color and, from Examples 34 to 42, that chromaticness is decreased by adding a clear color.

Furthermore, Examples in other polymerizable monomers, photopolymerization catalysts and specific pigments are shown in Table 5 and 6 below.

TABLE 5

| | Color Tone | UDMA | DPH | BisGMA | NPG | 3G | TMPT | APO | CQ | DMBE | R972 |
|---|---|---|---|---|---|---|---|---|---|---|---|
| Example 43 | Cyan | 60 | — | 10 | 30 | | — | 1.5 | 0.5 | 1 | 8 |
| Example 44 | Cyan | — | 60 | 10 | 30 | | — | 2 | 0.5 | 1 | 9 |
| Example 45 | Cyan | — | — | 40 | 60 | | — | 1 | 0.5 | 1 | 7 |
| Example 46 | Cyan | 60 | 10 | — | — | 30 | — | 2 | 0.3 | 2 | 10 |
| Example 47 | Magenta | — | 70 | — | — | 30 | — | 2 | 0.5 | 2 | 6 |
| Example 48 | Magenta | — | — | 30 | — | 70 | — | 3 | 0.3 | 1 | 8 |
| Example 49 | Magenta | 70 | — | — | — | — | 30 | 1 | 0.6 | 3 | 8 |
| Example 50 | Yellow | — | 70 | — | — | — | 30 | 2 | 0.75 | 2 | 9 |
| Example 51 | Yellow | — | — | 30 | — | — | 70 | 2 | 1 | 1 | 8 |
| Example 52 | Yellow | 70 | — | — | 30 | — | — | 2 | 1 | | 9 |
| Example 53 | Cyan | 70 | — | — | 30 | — | — | — | 0.5 | 3 | 9 |
| Example 54 | Cyan | 70 | — | — | 30 | — | — | 2 | — | 2 | 9 |
| Example 55 | Magenta | 70 | — | — | 30 | — | — | 2 | — | 2 | 9 |
| Example 56 | Yellow | 70 | — | — | 30 | — | — | 2 | — | 2 | 9 |

| | Pigment | | | | |
|---|---|---|---|---|---|
| | Phthalocyanine Blue | | Quinacridone | Quinacridone | Benzimidazolone | Disazo |
| | P.B 15:3 | P.B 15 | Magenta | Red | Yellow HG | Yellow GR |
| Example 43 | 0.75 | — | — | — | — | — |
| Example 44 | 0.75 | — | — | — | — | — |
| Example 45 | 0.75 | — | — | — | — | — |
| Example 46 | 0.75 | — | — | — | — | — |
| Example 47 | — | — | 0.75 | — | — | — |
| Example 48 | — | — | 0.75 | — | — | — |
| Example 49 | — | — | 0.75 | — | — | — |
| Example 50 | — | — | — | — | 0.75 | — |
| Example 51 | — | — | — | — | 0.75 | — |
| Example 52 | — | — | — | — | 0.75 | — |
| Example 53 | — | 0.75 | — | — | — | — |
| Example 54 | — | 0.75 | — | — | — | — |
| Example 55 | — | — | — | 0.75 | — | — |
| Example 56 | — | — | — | — | — | 0.75 |

TABLE 6

| | Color Tone | L*a*b* color system | | | Munsell color system | | |
|---|---|---|---|---|---|---|---|
| | | L* | a* | b* | H | V | C |
| Example 43 | Cyan | 54.3 | −28.54 | −41.1 | 5.8B | 5.27 | 11.8 |
| Example 44 | Cyan | 54.35 | −25.38 | −45.5 | 7.0B | 5.27 | 12.51 |
| Example 45 | Cyan | 55.27 | −26.55 | −44.21 | 6.6B | 5.37 | 12.32 |
| Example 46 | Cyan | 55.41 | −29.97 | −38.95 | 5.3B | 5.38 | 11.51 |
| Example 47 | Magenta | 51.21 | 58.69 | −19.25 | 2.5RP | 4.96 | 14.47 |
| Example 48 | Magenta | 51.31 | 61.75 | −22.21 | 2.4RP | 4.97 | 14.84 |
| Example 49 | Magenta | 51.57 | 60.78 | −20.86 | 2.3RP | 5.0 | 14.33 |
| Example 50 | Yellow | 89.01 | −11.73 | 89.96 | 7.4Y | 8.79 | 12.21 |
| Example 51 | Yellow | 89.93 | −13.03 | 92.26 | 7.8Y | 8.88 | 12.5 |
| Example 52 | Yellow | 90.44 | −11.88 | 65.42 | 7.5Y | 8.93 | 9.77 |
| Example 53 | Cyan | 69.56 | −32.96 | −19.7 | 1.5B | 6.8 | 8.49 |
| Example 54 | Cyan | 69.62 | −29.53 | −23.04 | 3.2B | 6.8 | 8.48 |
| Example 55 | Magenta | 59.57 | 41.55 | 3.95 | 8.0RP | 5.79 | 10.03 |
| Example 56 | Yellow | 72.84 | −1.45 | 85.24 | 4.7Y | 7.13 | 11.99 |

It is seen from Examples 43 to 53 that the objective cyan, magenta or yellow color is obtained by which polymerizable monomer and photopolymerization catalyst are used. It is also seen that a cyan, magenta or yellow color is obtained even when using preferred other pigments.

In the methods for the measurement of a yield viscosity and a thixotropy index of a paste, STRESSTECH Rheometer manufactured by Rheologica Instruments was used.

The measurement conditions are shown below.
1) A cone plate-plate jig having a diameter of 40 mm and an angle of 4° is set so as to adjust a space between samples to 0.0 mm.
2) The measurement conditions are controlled to a temperature of 23° C. under the atmospheric pressure.
3) An initiation stress is measured at 1.00E+1 Pa.
4) A viscosity is measured at a frequency of 10 to 1 [Hz].
5) After double logarithmic plotting with a viscosity as the vertical ordinate and a frequency as the horizontal ordinate, a thixotropy ratio is calculated by dividing a maximum value of the viscosity by a minimum value. It is determined that the sample having a ratio is 1.1 has a "thixotropic nature".

Figure 3:
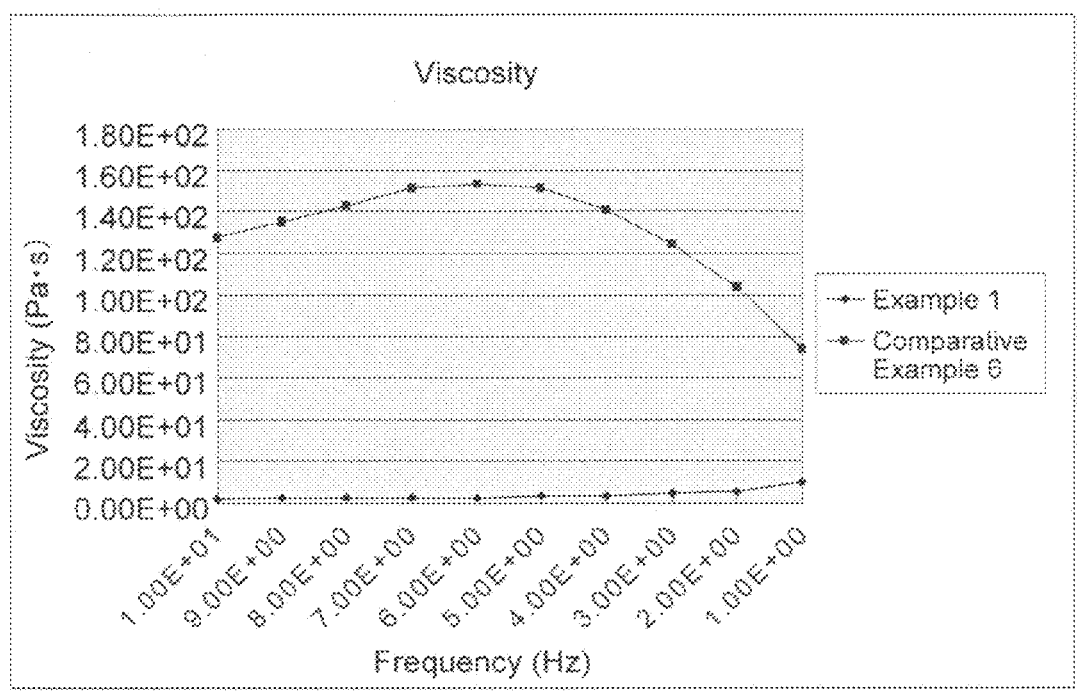
FIG. 3 shows a graph in which the logarithm of a viscosity is plotted against a frequency.

The numerical value obtained by logarithmic plotting of the measurement results of the viscosity is shown in Table 7, and a graph is shown in FIG. 3.

TABLE 7

| Frequency (Hz) | Viscosity (Pa · s) | |
|---|---|---|
| | Example 1 | Comparative Example 6 |
| 10.00 | 1.83 | 127.60 |
| 9.00 | 2.70 | 134.90 |
| 8.00 | 2.52 | 143.20 |
| 7.00 | 2.91 | 151.40 |
| 6.00 | 2.92 | 153.80 |
| 5.00 | 3.36 | 151.50 |
| 4.00 | 3.54 | 140.80 |
| 3.00 | 4.48 | 124.50 |
| 2.00 | 5.14 | 104.20 |
| 1.00 | 10.16 | 73.86 |

As is apparent from the results shown in FIG. 3, the visible light-polymerizable dental composition (Example 1) of the present invention is a low viscosity type dental composition having a thixotropic nature which is excellent in paste operability.

The dental composition, more particularly the dental composition which is mixable, is preferably a paste type and is capable of freely reproducing a color tone, and a set thereof of the present invention can be used for all kinds of dental materials (for example, fillers, temporary crowns, dental prostheses, implant upper structures, facing crowns and the like) produced from various materials (for example, composite materials, resins, ceramics and the like) which can be used in the dental field. The dental composition can also be directly applied to natural teeth.

What is claimed is:

1. A dental coloring material set comprising a combination of:
    (1) a dental coloring material composition comprising:
        (a) a polymerizable monomer and/or an oligomer,
        (b) a polymerization catalyst, and
        (c) a pigment and/or a dye, wherein
        the composition is a mixed paste, and
        a color tone thereof is a cyan color based on three subtractive primary colors,
        wherein when the cyan color is tone-evaluated by a Munsell color system, measured values at a white back of a specimen having a thickness of 0.1 mm are as follows: hue (H) of 5PB to 1PB, 10B to 1B, 10GB to 5GB, value of color (V) of 2 to 9, and chromaticness (C) of 6 to 15,
    (2) a dental coloring material composition comprising:
        (a) a polymerizable monomer and/or an oligomer,
        (b) a polymerization catalyst, and
        (c) a pigment and/or a dye, wherein
        the composition is a mixed paste, and
        a color tone thereof is a magenta color based on three subtractive primary colors,
        wherein when the magenta color is tone-evaluated by a Munsell color system, measured values at a white back of a specimen having a thickness of 0.1 mm are as follows: hue (H) of 1R, 10RP to 1RP, 10P to 5P, value of color (V) of 2 to 9, and chromaticness (C) of 6 to 17, and
    (3) a dental coloring material composition comprising:
        (a) a polymerizable monomer and/or an oligomer,
        (b) a polymerization catalyst, and
        (c) a pigment and/or a dye, wherein
        the composition is a mixed paste, and
        a color tone thereof is a yellow color based on three subtractive primary colors,
        wherein when the yellow color is tone-evaluated by a Munsell color system, measured values at a white back of a specimen having a thickness of 0.1 mm are as follows: hue (H) of 1Y to 10Y, 1GY to 2GY, value of color (V) of 4 to 10, and chromaticness (C) of 7 to 17, wherein at least two compositions selected from the group consisting of compositions (1), (2) and (3) are mixed upon use, wherein each composition (1), (2) and (3) has a viscosity of 1 to 20 Pa·S as measured in a cone plate-plate system at a frequency sweep of 7 to 1 Hz, an initiation stress of 1.00E+1 Pa and a temperature of 23° C., and wherein the polymerization catalyst of compositions (1), (2) and (3) is independently selected from the group consisting of benzophenone, diacetil, benzil, 4,4'-dimethoxybenzil, 4,4'-oxybenzil, 4,4'-chlorobenzil, camphorquinone, camphorquinonecarboxylic acid, 2,3-pentadion, 2,3-octadion, 9,10-phenanthrenequinone, acenaphthenequinone, 2,4,6-trimethylbenzoyldiphenylphosphine oxide, 2,6-dimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, methyl 2,4,6-trimethylbenzoylphenylphosphinate, ethyl 2,4,6-trimethylbenzoylphenylphosphinate, phenyl 2,4,6-trimethylbenzoylphenylphosphinate, a diacyl peroxide, a peroxyester, a dialkyl peroxide, a peroxyketal, a ketone peroxide, and a hydroperoxide.

2. The dental coloring material set as defined in claim 1, further comprising:
(4) a white-colored composition comprising:
(a) a polymerizable monomer and/or an oligomer,
(b) a polymerization catalyst, and
(c) a pigment and/or a dye,
wherein at least two compositions selected from the group consisting of compositions (1), (2) (3) and (4) are mixed upon use.

3. The dental coloring material set as defined in claim 1, further comprising:
(5) a black-colored composition comprising:
(a) a polymerizable monomer and/or an oligomer,
(b) a polymerization catalyst, and
(c) a pigment and/or a dye,
wherein at least two compositions selected from the group consisting of compositions (1), (2), (3) and (5) are mixed upon use.

4. The dental coloring material set as defined in claim 1, further comprising:
(4) a white-colored composition comprising:
(a) a polymerizable monomer and/or an oligomer,
(b) a polymerization catalyst, and
(c) a pigment and/or a dye, and
(5) a black-colored composition comprising:
(a) a polymerizable monomer and/or an oligomer,
(b) a polymerization catalyst, and
(c) a pigment and/or a dye,
wherein at least two compositions selected from the group consisting of compositions (1), (2), (3), (4) and (5) are mixed upon use.

5. The dental coloring material set according to any one of claims 1 to 4, which further comprises:
(6) a transparent composition comprising:
(a) a polymerizable monomer and/or an oligomer, and
(b) a polymerization catalyst.

6. A method for applying the dental coloring material set according to claim 1, which comprises mixing at least two compositions selected from the group consisting of compositions (1), (2) and (3) to prepare any color tone composition, and applying the color tone composition to a dental material as a dental coloring material.

7. The dental coloring material set according to any one of claims 1 to 4, wherein at least one composition of the set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

8. The method according to claim 6, wherein at least one composition (1), (2) and (3) of the set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

9. A method for applying the dental coloring material set according to claim 2, which comprises mixing at least two compositions selected from the group consisting of compositions (1), (2), (3) and (4) to prepare any color tone composition, and applying the color tone composition to a dental material as a dental coloring material.

10. The method according to claim 9, wherein each composition of the dental coloring material set has a viscosity of 1 to 20 Pa·S as measured in a cone plate-plate system at a frequency sweep of 7 to 1 Hz, an initiation stress of 1.00E+1 Pa and a temperature of 23° C.

11. The method according to claim 9, wherein at least one composition of the dental coloring material set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

12. A method for applying the dental coloring material set according to claim 3, which comprises mixing at least two compositions selected from the group consisting of compositions (1), (2), (3) and (5) to prepare any color tone composition, and applying the color tone composition to a dental material as a dental coloring material.

13. The method according to claim 12, wherein each composition of the dental coloring material set has a viscosity of 1 to 20 Pa·S as measured in a cone plate-plate system at a frequency sweep of 7 to 1 Hz, an initiation stress of 1.00E+1 Pa and a temperature of 23° C.

14. The method according to claim 12, wherein at least one composition of the dental coloring material set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

15. A method for applying the dental coloring material set according to claim 4, which comprises mixing at least two compositions selected from the group consisting of compositions (1), (2) ,(3), (4) and (5) to prepare any color tone composition, and applying the color tone composition to a dental material as a dental coloring material.

16. The method according to claim 15, wherein each composition of the dental coloring material set has a viscosity of 1 to 20 Pa·S as measured in a cone plate-plate system at a frequency sweep of 7 to 1 Hz, an initiation stress of 1.00E+1 Pa and a temperature of 23° C.

17. The method according to claim 15, wherein at least one composition of the dental coloring material set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

18. A method for applying the dental coloring material set according to claim 5, which comprises mixing at least two compositions selected from the group consisting of compositions (1), (2), (3), (4), (5) and (6) to prepare any color tone composition, and applying the color tone composition to a dental material as a dental coloring material.

19. The method according to claim 18, wherein each composition of the dental coloring material set has a viscosity of 1 to 20 Pa·S as measured in a cone plate-plate system at a frequency sweep of 7 to 1 Hz, an initiation stress of 1.00E+1 Pa and a temperature of 23° C.

20. The method according to claim 18, wherein at least one composition of the dental coloring material set further comprises (d) a filler having a particle diameter of 0.001 to 0.1 μm, and the at least one composition has a viscosity of 1 to 15 Pa·S as measured in a cone plate-plate system at a frequency sweep of 7 to 1 Hz, an initiation stress of 1.00E+1 Pa and a temperature of 23° C., and also has a thixotropic nature in which a ratio of a minimum value to a maximum value of a viscosity is 1.1 or more at a frequency of 7 to 1 Hz.

21. The dental coloring material set as defined in claim 1, wherein the polymerization catalyst of compositions (1), (2) and (3) is independently selected from the group consisting of camphorquinone and 2,4,6-trimethylbenzoyldiphenylphosphine oxide.

\* \* \* \* \*